United States Patent [19]

Steen

[11] Patent Number: 4,915,501
[45] Date of Patent: Apr. 10, 1990

[54] DEVICE FOR MEASURING THE LIGHT SCATTERING OF BIOLOGICAL CELLS IN FLOW CYTOPHOTOMETERS

[76] Inventor: Harald Steen, Wolffs gate 3, N-0358, Oslo 3, Norway

[21] Appl. No.: 43,552
[22] PCT Filed: Jul. 11, 1986
[86] PCT No.: PCT/NO86/00051
§ 371 Date: Mar. 6, 1987
§ 102(e) Date: Mar. 6, 1987
[87] PCT Pub. No.: WO87/00628
PCT Pub. Date: Jan. 29, 1987

[30] Foreign Application Priority Data
Jul. 16, 1985 [NO] Norway .................................. 852836

[51] Int. Cl.⁴ ............................................. G01N 21/00
[52] U.S. Cl. ..................................... 356/343; 356/338
[58] Field of Search ................. 356/73, 336, 337, 338, 356/339, 340, 341, 343

[56] References Cited

U.S. PATENT DOCUMENTS 3,563,660  2/1971  Soloway et al. ..................... 356/336
4,188,121  2/1980  Hirleman et al. .................... 356/336
4,286,876  9/1981  Hogg et al. .......................... 356/343

FOREIGN PATENT DOCUMENTS 0140616  5/1985  European Pat. Off. .............. 356/73

OTHER PUBLICATIONS

Steen et al, "Differential of Light-Scattering Detection in an Arc-Lamp-Based Epi-Illumination Flow Cytometer", *Cytometry* 6 (1985), pp. 281-285.

*Primary Examiner*—Richard A. Rosenberger
*Attorney, Agent, or Firm*—Cushman, Darby & Cushman

[57] ABSTRACT

A device which enables the measurement of light scattering from microscopical particles and biological cells in two different regions of scattering angle in flow cytometers where the particles/cells are illuminated through microscope optics (4) having high numerical aperture. A dark field image (2) of the particles/cells is formed on a slit (7) behind which is situated a telescope (10) which reproduces the angle distribution of the scattered light from the particles/cells. Light scattered from large angles (>15°) is separated from the light field behind this telescope by means of a mirror (13) in the central part of this light field reflecting the light into a first detector (14) while the remaining light which is dominated by small scattering angles falls on another detector (15).

4 Claims, 2 Drawing Sheets

DEVICE FOR MEASURING THE LIGHT SCATTERING OF BIOLOGICAL CELLS IN FLOW CYTOPHOTOMETERS

The present invention concerns a device for simultaneous measurement of two angle components of the light scattering of biological cells or particles in flow cytometers comprising a microscope condenser with high numerical aperture containing a central field stop means which produces a conical dark field in the illumination field of said condenser, and a microscope objective with its light opening within said dark field and its object plane in common with the object plane of the condenser.

More precisely, the device facilitates measuring of the light scattering of biological cells and other microscopical particles in two different regions of light scattering angles as the cells or particles pass one by one through the measuring area of the flow cytophotometer. Because the light scattering within the respective angle regions depends on different characteristics of the cell/particle, viz. on one side the size (volume) and on the other side submicroscopical structure, such a device may be used to characterize and identify cells/particles which are different with regard to these characteristics.

Flow cytometry is a method which has numerous applications within various fields of cell biology, medicine as well as measurements of nonbiological particles of almost any material. In a flow cytometer photometrical signals from individual particles of microscopical size are measured as they, carried by a laminar flow of fluid, pass one by one through a focus of excitation light of high intensity. The particles are centered in the liquid flow by so called hydrodynamic focusing. The photometrical signals that can be measured are 1) the fluorescence of the particles/cells, 2) the light scattering of the the particles/cells, and 3) the light absorption of the the particles/cells. In particular the former two of these of types of signals have proved to be very informative.

A typical example of an application of flow cytometry is the measurement of the contents of individual cells of different components such as DNA and protein. The cells are stained for this purpose with a fluorescent dye which binds specifically and quantitively to the respective component. Each cell which passes through the excitation focus of the instrument thus produces a pulse of fluorescence. This light is collected by appropriate optics and recorded by a light detector. The electrical impulses from this detector, which are proportional with the amount of dye of the cells and thus proportional with the content of the respective cell component, are measured and stored according to their size in an electronic memory—a so-called multichannel pulse height analyzer. In this way it is possible to measure several thousand cells per second with high precision. Thus, a histogram showing the number of cells as a function of their content of the respective component is accumulated.

The excitation light scattered by the cell as it passes through the focus of the instrument may be recorded by a second detector. Depending on the scattering angle the signal carries information about the cross-section or volume of the cell as well as its structure and density.

In some flow cytometers the excitation light is produced by a laser. The fluid flow which carries the particles passes through the laser beam. The flourescence and light scattering of the particles are detected through two separate optical systems situated laterally of the laser beam. In certain types of such flow cytophotometers the flow is a jet in air. In other instruments the fluid flow passes through a closed chamber.

In such flow cytometers the light scattering may be measured both at large and small scattering angles by detectors situated at different agles to the laser beam. For particles with sizes and refractive index similar to that of biological cells (diameter 1–30 $\mu$m) the light scattering at small scattering angles will be dominated by refraction from the surface of the particles and may thus be taken as a measure of the size of the particles. The light scattering at angles larger than about 10°, on the other hand, will be associated with structures having dimensions smaller than the wave length of light. Simultaneous measurement of light scattering at small and large scattering angles in such flow cytometers has proven very useful as a method to identify different types of biological cells, in particular different types of white blood cells, such as leukocytes.

In a different type of flow cytometers a high pressure arc lamp, typically containing mercury, is used to produce the excitation light. Such instruments have several significant advantages in addition to the fact that they are less expensive than instruments using lasers. However, with such lamp-based flow cytometers it has not been possible to measure the light scattering in different regions of scattering angle. This is due to the fact that the excitation is carried through microscope optics with high numerical aperture and furthermore that the flow chamber does not allow the measurement of light scattering.

A known flow chamber (Norwegian patent nr. 144002) in combination with a new system for dark field detection (Norwegian patent nr. 145176) makes it possible to measure the light scattering in a lamp based flow cytometer. The present invention is a further development of this system which facilitates simultaneous detection of the light scattering in two different regions of scattering angle.

The present invention is based on three characteristics of the light scattering of biological cells, viz. 1) that the intensity of the scattered light at small scattering angles ($<10°$) is much larger that the combined intensity at all other angles, 2,) that the scattered light at small scattering angles is produced mainly by diffraction from the cell surface (contour), and 3) that the light scattering at larger angles ($<15°$) is dominating by scattering from submicroscopical structures, i.e. structures smaller than the wavelenght of light, and that this light scattering is approximately independent of the scattering angle.

According to this invention the device mentioned in the introduction is characterized in that the dark field is reproduced behind the image plane of the microscope objective by means of a telescope (10) so that the light in the central part of the said dark field is reflected towards a light detector by means of a mirror and is thereby separated from the light in the peripherial part of the said dark field which falls on another light detector.

Further characteristics of the device according to the invention will be appear from the subsequent claims as well as from the following description with reference to the accompanying figures.

Figure 1:
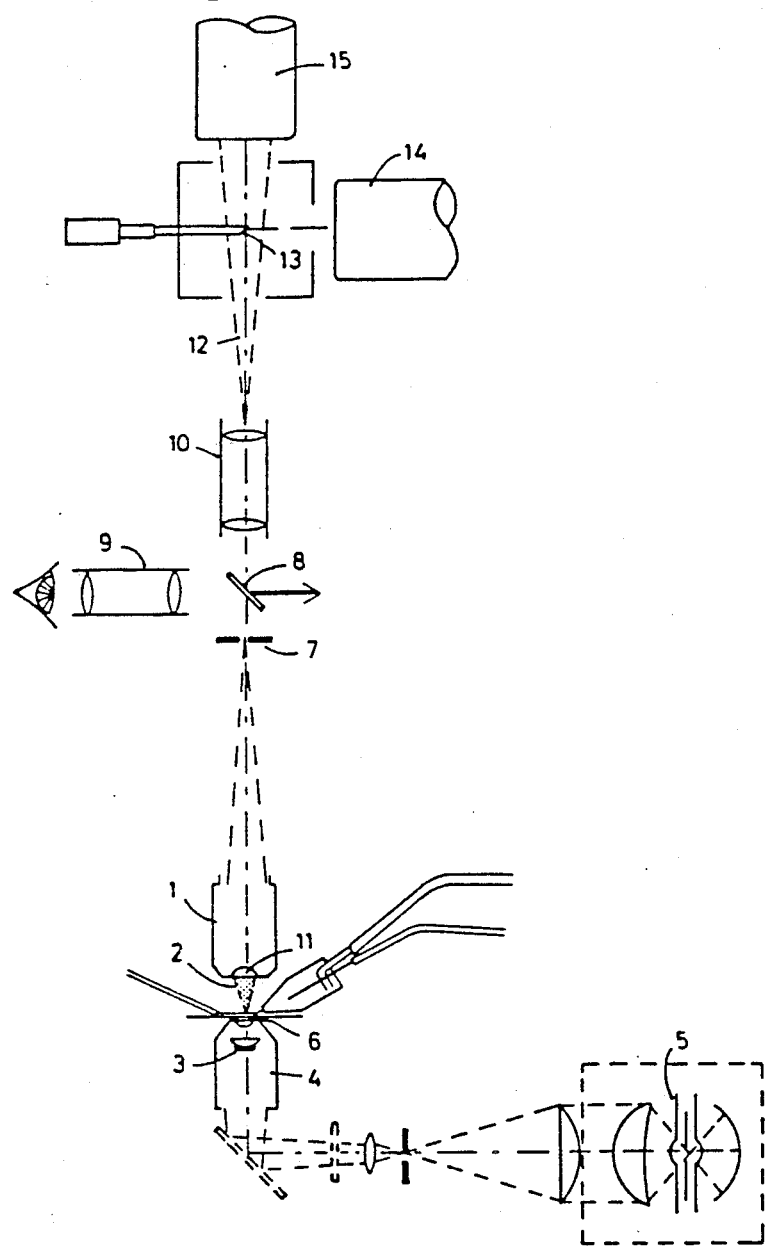
FIG. 1 shows how the device according to the invention enables detection in two different regions of scattering angle.

The scattered light is measured through the microscope objective 1 within the dark field 2 which is produced by an obscuration 3 (central field stop means) in the microscope condenser 4 which focuses the excitation light from the lamp 5 onto the particle flow 6. The microscope objective 1 is focused on the particle flow 6 so that an image of the particle flow is formed on the slit 7. The slit 7 eliminates light from those parts of the object plane which do not contain the particle flow and thereby increases the signal to noise ratio in the measurement. A 45° mirror 8 can be inserted behind the slit 7 so that the dark field image of the particle flow 6, i.e. the particle flow seen in scattered light, may be observed through an ocular 9. All of this is described in Norwegian patent nr. 145176, which also includes a light detector immediately behind the slit 7.

Figure 2:
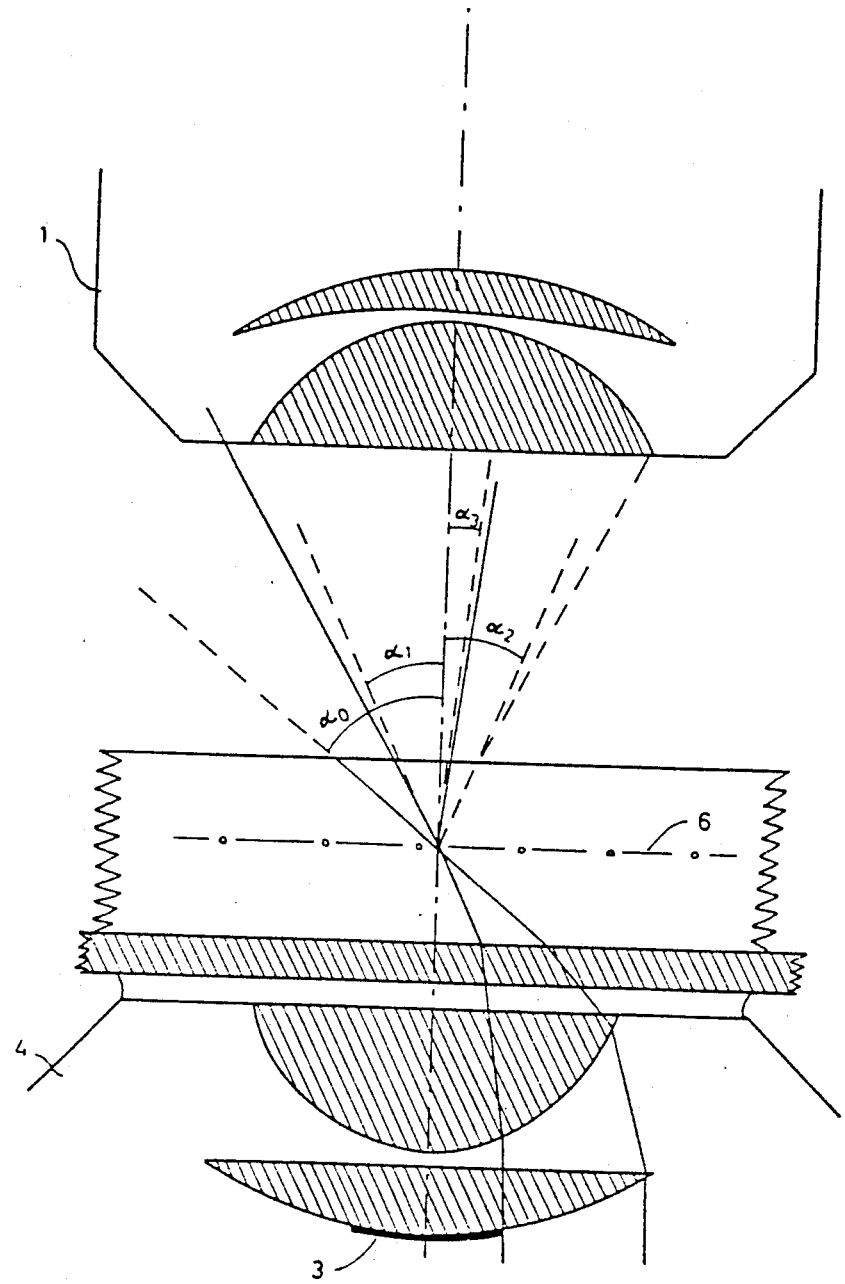
FIG. 2 illustrates how the different parts of the dark field contain light from different scattering angles.

As shown in FIG. 2 the different parts of the dark field contain light of different scattering angles. Thus, the peripheral part of the dark field contains light scattered over the angle region from $\alpha_0 + \alpha_2$, while the central part of the dark field, that is, the region immediately surrounding the optical axis, contains light from the angle region from $\alpha_1$ to $\alpha_0$. The size of the field stop means 3 is such that $\alpha_1$ is 1°–2° larger than $\alpha_2$. $\alpha_2$ is determined by the numerical aperture of the secondary objective 1. A suitable numerical aperture for the objectiv 1 is N.A.=0.4, which gives $\alpha_2, = 18$°.

A telescope 10 which is situated behind the slit 7 produces an image of aperture (pupil) 11 of the objective 1 at infinity. This means that the conical light beam 12 leaving the telescope 10 is a reproduction of the dark field 2. The angle distribution of the light intensity within the light beam 12 will therefore be identical to that of dark field 2. The central part of the light beam 12, which contains light scattered to larger angles than about 15° is separated from the rest of the light beam 12 by means of the mirror 13 which forms an angle of 45° with the optical axis of the objective 1. The light falling on this mirror is reflected toward a light detector 14 which thus measures light scattered to larger angles than about 15° while the remaining light falls on an other detector 15 which thereby detects light scattered primarily to small angles. Each cell/particle which passes through the measuring area of the flow cytometer will thereby give rise to an electrical pulse from each of the two detectors 14 and 15. These pulses represent the two components of the scattered light which is the purpose of the present invention.

I claim:

1. A flow cytometer device for simultaneous measurement of two angle components of light scattering from biological cells or particles comprising:
   a microscope condenser having a high numerical aperture containing a central field stop means for producing a conical dark field in an illumination field of said condenser;
   a microscope objective having an aperture disposed within said dark field and having an object plane in common with an object plane of the condenser, the dark field having an axis of symmetry in common with the optical axis of the objective and the condenser, and the dark field extending at an angle of at least 15° around said axis of symmetry, the entrance aperture of said objective as seen from the object plane of this objective extending over an angle which is 1°–2° smaller than the angle extended by the dark field and is thus situated entirely within said dark field;
   telescope means for reproducing the dark field behind an image plane of the microscope objective;
   mirror means for reflecting a central portion of said reproduced dark field;
   a first light detector for receiving light reflected by said mirror means; and
   a second light detector for receiving light in the peripheral portion of said dark field,
   whereby, scattered light at small scattering angles produced by defraction from the cell or particle surface are separated from light scattered at larger angles from structures other than the cell surface.

2. A device according to claim 1, wherein the condenser focuses light from an intense light source toward its object plane through which biological cells or particles carried by a microscopical, laminar flow of fluid are passing.

3. A device according to claim 1, wherein an adjustable slit is disposed in the image plane of said objective, said slit being set so as to cover that part of the image produced by the objective which contains the image of the particle flow where said flow passes through the common optical axis of the objective and condenser, said slit eliminating light from those parts of the object plane which do not contain particle flow.

4. A device according to claim 1, wherein a telescope is situated behind the slit and produces an image of the aperture (pupil) of the objective at infinity behind the telescope from which extends a light beam where the angle distribution of the light intensity corresponds exactly to that which can be observed within the dark field.

* * * * *